United States Patent [19]

Lagow

[11] 4,453,028

[45] Jun. 5, 1984

[54] PERFLUORINATED COMPOUNDS WITH CYCLOHEXYL GROUPS

[76] Inventor: Richard J. Lagow, 6204 Shadow Mountain Dr., Austin, Tex. 78731

[21] Appl. No.: 363,112

[22] Filed: Mar. 29, 1982

[51] Int. Cl.³ .............................................. C07C 19/08
[52] U.S. Cl. .................................. 570/130; 570/131; 252/302
[58] Field of Search ........................ 570/131, 130, 129

[56] References Cited

U.S. PATENT DOCUMENTS

| | | | |
|---|---|---|---|
| 2,606,212 | 8/1952 | McBee et al. | 570/131 |
| 2,653,912 | 9/1953 | Ross et al. | 570/129 |
| 3,293,305 | 12/1966 | Haszeldine et al. | 570/129 |
| 3,911,138 | 10/1975 | Clark | 424/352 |

Primary Examiner—Charles F. Warren
Assistant Examiner—Joseph A. Boska
Attorney, Agent, or Firm—Hamilton, Brook, Smith & Reynolds

[57] ABSTRACT

This invention relates to perfluorinated compounds with cyclohexyl groups. Such compounds are useful as synthetic blood substitutes and perfusion media, and for other purposes, and in emulsions which contain such compounds. A method is disclosed for direct fluorination without creating excessive unwanted byproducts. Hydrocarbon starting compounds used in this invention may be purchased or synthesized. The compounds created by the methods of this invention include perfluorinated tetraphenylmethane, perfluorinated diphenylmethane, and perfluorinated t-butylcyclohexane.

2 Claims, 1 Drawing Figure

PERFLUORINATED COMPOUNDS WITH CYCLOHEXYL GROUPS

GOVERNMENT SUPPORT

The invention described herein was supported in whole or in part by the U.S. Air Force Office of Scientific Research.

TECHNICAL FIELD

This invention is in the fields of chemistry and biology, and more particularly fluorocarbon chemistry and blood substitutes.

BACKGROUND ART

Several synthetic fluorocarbon compounds are known to be useful as blood substitutes. Such compounds are described in U.S. Pat. No. 3,911,138 (Clark, 1975), which describes emulsions that contain perfluorinated cyclic hydrocarbons, and U.S. Pat. Nos. 4,110,474 and 4,187,252 (Lagow et al, 1978 and 1980), which describe emulsions that contain perfluorotetramethyl pentane. However, continuing work is being done to create and identify other compounds which are also suitable as blood substitutes, perfusion media, breathable liquids, and for other biological and chemical purposes. Such compounds are likely to have superior qualities regarding one or more relevant characteristics, which include: oxygen affinity and release, solubility or emulsifiability in various media, low toxicity, high shelf life, appropriate stability within the body, low retention within vital organs of the body, and low cost of manufacture.

As used herein, the prefix "perfluoro-" and the term "perfluorinated" indicate that all or essentially all of the replaceable atoms (such as hydrogen) in a compound have been replaced by fluorine atoms. As used herein, the term "hydrocarbon" refers to molecules that contain hydrogen and carbon atoms, regardless of whether they also contain oxygen, fluorine or other atoms.

DISCLOSURE OF THE INVENTION

This invention relates to novel organic compounds which are useful as synthetic blood substitutes and perfusion media, and for other purposes. This invention also relates to emulsions and other mixtures which contains such compounds, and to processes for preparing such compounds.

More particularly, this invention relates to compounds that contain perfluorinated cyclohexyl groups, which have the following general formula:

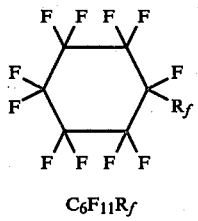

$C_6F_{11}R_f$ where $R_f$ represents a fluorine-containing organic group.

The compounds of this invention may contain more than one cyclohexyl structure bonded to an organic group.

The method of this invention comprises at least two steps, and may include at least one additional step of purification. The first step comprises obtaining, by synthesis or by selection, a branched hydrocarbon ether compound with carbon and oxygen atoms in the desired configuration. If the hydrocarbon ether thus obtained contains significant quantities of impurities, byproducts, or other undesired compounds, then a purification step may be preferred. A necessary third step involves perfluorinating the hydrocarbon ether compound. If desired, another purification step may be performed after perfluorination. If desired, the resulting perfluorinated branched ether may be mixed with solvents, saline solutions or aqueous solutions, or other fluids to increase its usefulness as a blood substitute, perfusion media, or breathable liquid, or for other biological or chemical purposes.

The products described herein have been created and analyzed by chemical techniques. Although biological testing is not yet complete, it is believed that these compounds are relatively nontoxic and useful as blood substitutes.

Figure 1:
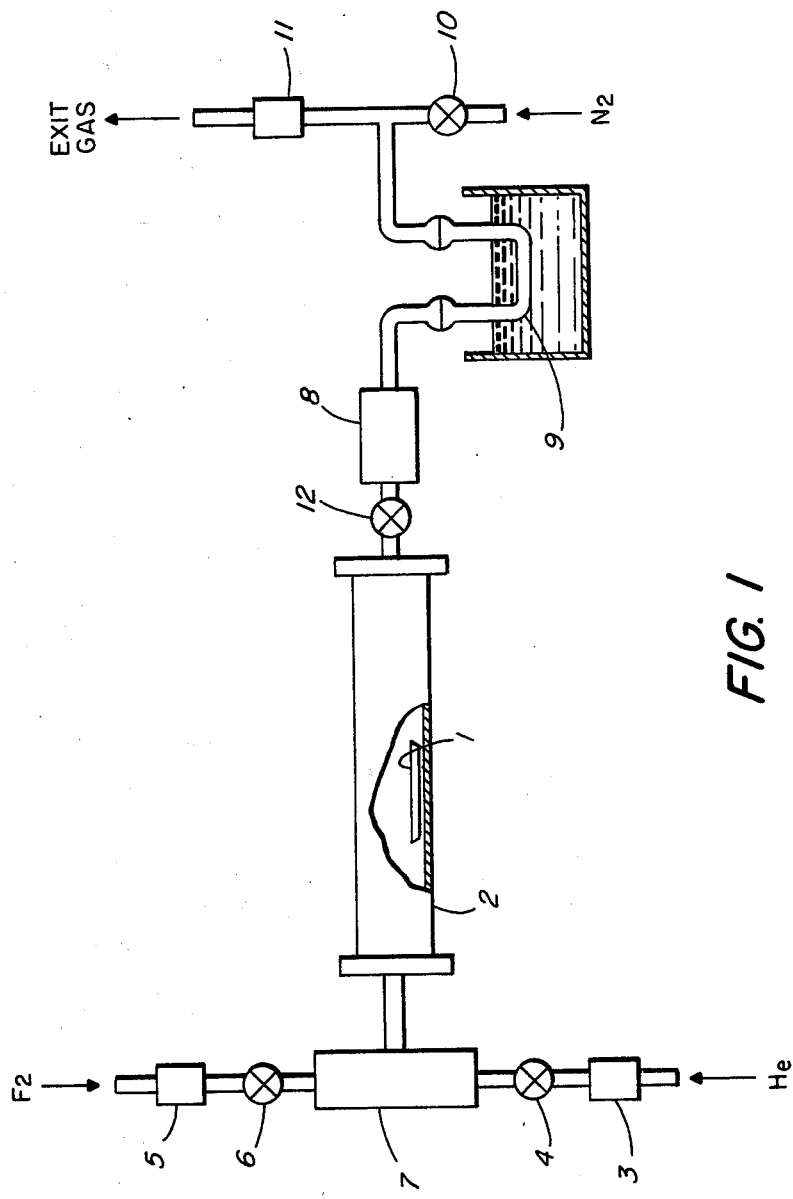
FIG. 1 is a simplified representation of a perfluorination system.

The compounds of this invention are created by the perfluorination of a hydrocarbon compound with an aromatic or cyclohexyl ring structure. Such perfluorination must be performed under carefully controlled conditions that prevent or minimize the opening, fragmentation or rearrangement of the molecules being perfluorinated. The hydrocarbon compounds that are perfluorinated by the method of this invention may be purchased, if commercially available, or synthesized. If desired, the compounds of this invention may be concentrated or purified by techniques which are known to those skilled in the art, including various types of distillation, chromatography, and crystallization.

BEST MODE OF CARRYING OUT THE INVENTION

One preferred mode of carrying out the method of this invention involves the perfluorination of selected hydrocarbon compounds which are commercially available. Such hydrocarbon compounds include tetraphenylmethane ($C(C_6H_5)_4$), diphenylmethane ($H_2C(C_6H_5)_2$), and t-butyl cyclohexane (($CH_3)_3C(C_6H_{11})$).

The compounds of this invention are synthesized by perfluorinating the selected cyclohexyl compounds 1. This may be done by careful application of direct fluorination in a cooled reactor system. Direct fluorination of hydrocarbons is a very exothermic reaction, and care must be taken to avoid fragmenting the molecules being fluorinated. To reduce fragmentation, fluorine is introduced slowly and at low temperatures. This procedure can be briefly summarized as follows, using a typical reaction system as shown in FIG. 1. This type of system is described in U.S. Pat. Nos. 4,113,345; 4,187,252; and 4,281,119 (Lagow et al).

The main reaction chamber 2 consists of a cylinder made of nickel, Monel alloy, or other material which resists fluorine attack. The hydrocarbon material which is to be fluorinated, if solid or liquid, may be loaded into shallow tray 1 often called a boat, which is placed inside reaction chamber 2. If the material is a solid, it may be ground or meshed into a powder, to increase the surface area available for contact with fluorine gas. If the material is a liquid, it may be vaporized and caused to condense on chilled copper turnings or other packing material inside reaction chamber 2. The temperature of the chamber may be controlled by various means, such as contacting the exterior of the chamber, or limited portions thereof, with hot or cold liquids.

An inert gas such as helium is used to flush all oxygen and other reactive molecules out of reaction chamber 2 before the reaction begins. The helium enters the chamber through flow meter 3 (for example, Metheson Gas Model 600 flowmeter) and metering valve 4. After the chamber is thoroughly flushed, the helium flow is stabilized, and reactor chamber 2 is cooled to a desired temperature.

Fluorine is added to chamber 2 by means of flowmeter 5 (for example, Hastings Model LF50X flowmeter) and metering valve 6. The helium and fluorine mix together in mixing chamber 7 before they contact the reactant. The fluorine flow is increased in a stepwise or gradual manner and the helium flow is decreased, until concentrated or pure fluorine is flowing through chamber 2. If desired, the system can be designed to accommodate elevated pressures.

When the fluorination reaction is complete, the fluorine flow is terminated and chamber 2 is flushed with helium if desired. The perfluorinated material is removed by removing tray 1 from chamber 2. Alternately, if the perfluorinated material was vaporized and condensed on copper turnings inside chamber 2, chamber 2 may be heated to a desired temperature, which increases the volatility of the perfluorinated compound. The compound vaporizes and is removed from chamber 2 by the continuing helium flow. The system may be fitted with a trap 8, which may be filled with a substance such as sodium fluoride (NaF) to remove HF from the exiting stream. This trap may be by passed while perfluorinated product is being removed from reactor 2.

The exiting gas stream passes through condensation trap 9. When volatile perfluorinated compounds are leaving chamber 2, trap 9 is immersed within a cold liquid, such as liquid nitrogen or a dry ice-isopropanol slush, to chill the trap. The compounds condense within the trap, which can be removed from the system by means of fittings.

The system may be fitted with a trap 11, containing an adsorbent compound such as alumina ($Al_2O_3$) to remove unreacted fluorine. The system may also be equipped with means for insuring that oxygen does not enter the system, such as a valve 10 to allow an inert gas such as nitrogen to enter the system at a slight pressure. The gas which exits trap 11 may travel through a substance such as mineral oil, which turns black if the gas contains fluorine; this indicates that the alumina in trap 11 should be replaced.

Perfluorination ideally indicates that every hydrogen or other replaceable atom has been replaced by a fluorine atom. However, in actual conditions, it may be difficult or impossible to replace every replaceable atom, or to detect whether every replaceable atom has in fact been replaced. Therefore, perfluorination is used herein in a non-ideal, functional sense to indicate that extensive fluorination has been performed with the purpose and practical effect of replacing the large majority or substantially all of the hydrogen or other replaceable atoms in a compound with fluorine atoms. For example, an analysis might indicate that the economically optimal material for a given use might be achieved by curtailing the fluorination reaction, thereby reducing expenses, at a given level of fluorination even though it is known that a small percentage of residual hydrogen atoms remain within the compound. Despite the presence of such residual hydrogen atoms, a highly-fluorinated compound of this nature should be regarded as "perfluorinated"; if created by the method of this invention, it would be within the scope of this invention.

Fluorocarbons are usually immiscible with blood; if injected into the body, fluorocarbons will coalesce into droplets which could clog blood vessels. To prevent this, fluorocarbons used as artificial blood are normally mixed with water as an emulsion. As used herein, an emulsion comprises a mixture of two immiscible liquids which also contains an emulsifying agent. In general, an emulsifying agent is a compound which prevents droplets in an emulsion from coalescing into larger droplets. Such emulsifying agents include a yolk-phospholipid which is known to be harmless in the body, and various types of polyoxyethylenes and polyoxypropylenes, which are suspected of causing reactions between proteins in the blood. Emulsions with controllable droplet or particle sizes can be created by conventional high-shear emulsifiers, e.g., the Manton-Gaulin homogenizer. Various forms of salt can be added to an emulsion to sustain a proper osmotic balance across cell membranes.

The liquid range of perfluorocyclohexyl compounds may occur at temperatures above 37° C. (normal body temperature). However, as part of a multi-component emulsion or fluorocarbon solution, perfluorocyclohexyl compounds may have utility and are currently under study. The perfluoro ring systems appear to be a favorable structural feature in fluorocarbons that dissolve oxygen; it is hypothesized that maximum oxygen solubility is obtained in fluorocarbon systems with bulky side groups which produce intermolecular interstices large enough to at least partially accommodate $O_2$.

EXAMPLE 1

Perfluorination of Tetraphenylmethane

Tetraphenylmethane (0.26 g), $C(C_6H_{11})_4$ was ground to a fine powder (100 mesh) and placed in a reaction chamber and contacted with helium and fluoring according to the reaction conditions listed in Table 1. 0.89 grams of the white solid, tetrakis (perfluorocyclohexyl)methane (96% yield) was recovered from the reactor. $^{19}F$ NMR in perfluorobenzene consisted of a broad multiplet centered at +124 ppm from $CFCl_3$ and a second multiplet at +180 from $CFCl_3$ which integrated for ten and one, respectively. Infrared analysis of a KBr disk gave absorptions at 1190 (broad), 1000 (m), 960 (m), 550 (w), 495 (w), and 470 (w) $cm^{-1}$. Mass spectral analysis gave a base peak of m/e 281 ($C_6F_{11}^+$) along with peaks at 855, 574, and 293 corresponding to the parent minus one, two, and three perfluorophenyls, respectively.

Elemental analysis for $C(C_6F_{11})_4$: Calculated: C, 26.4%; F, 73.6%; Observed: C 26.1%; F, 73.4%.

Melting point: 91°–92° C.

TABLE 1

| | Reaction Conditions | | |
|---|---|---|---|
| Temp. (°C.) | He (cc/min) | $F_2$ (cc/min) | Time (days) |
| −80 | 60 | 1.0 | 0.5 |
| −80 | 30 | 1.0 | 0.5 |
| −80 | 10 | 1.0 | 0.5 |

TABLE 1-continued

| Temp. (°C.) | Reaction Conditions | | Time (days) |
|---|---|---|---|
| | He (cc/min) | F$_2$ (cc/min) | |
| −80 | 0 | 1.0 | 1.0 |
| room | 0 | 1.0 | 1.0 |
| room | 0 | 5.0 | 3.0 |
| +50 | 0 | 2.0 | 3.0 |
| room | 60 | 0.0 | 1.0 |

EXAMPLE 2

Perfluorination of Diphenylmethane

Diphenylmethane (0.24 g) was placed in a reactor chamber and contacted with helium and fluorine according to the reaction conditions listed in Table 2. Bis(perfluorocyclohexyl) difluoromethane was obtained in 93% yield (0.72 g) by recrystallization in hexafluorobenzene (C$_6$F$_6$). $^{19}$F NMR of the product dissolved in C$_6$F$_6$ gave two broad multiplets centered around +120 and +180 ppm from CFCl$_3$ which integrated for eleven and one, respectively. Infrared analysis utilizing a KBr disk gave absorptions at 1180 (broad), 1000 (m), 960 (m), 500 (w), and 480 (w) cm$^{-1}$. The highest molecular weight fragment observed in the mass spectrum m/e 331, corresponded to the parent minus one perfluorophenyl. Freezing point depression of bis(perfluorocyclohexyl) difluoromethane in C$_6$F$_6$ gave a moleculr weight of 550 g/mol (theoretical: 612 g/mol).

Elemental analysis for C(C$_6$F$_{11}$)$_2$F$_2$: Calculated: C,25.5%, F, 74.5%; Observed: C, 25.7%, F 74.1%.

TABLE 2

| Temp. (°C.) | Reaction Conditions | | Time (days) |
|---|---|---|---|
| | He (cc/min) | F$_2$ (cc/min) | |
| −80 | 60 | 1.0 | 1.0 |
| −80 | 30 | 1.0 | 0.5 |
| −80 | 10 | 1.0 | 0.5 |
| −80 | 0 | 1.0 | 1.0 |
| room | 0 | 1.0 | 1.0 |
| room | 0 | 5.0 | 3.0 |
| +50 | 0 | 2.0 | 3.0 |
| room | 60 | 0.0 | 1.0 |

The solubility in C$_6$F$_6$ of the compounds described in Examples 1 and 2 facilitated their purification through recrystallization and allowed a check on their molecular weights by freezing point depression. The complex multiplet evidenced in the CF$_2$ region of the $^{19}$F NMR is expected in analogy with the large number of overlapping A-B systems seen in the spectrum of perfluoromethylcyclohexane. Nonetheless, integral ratios obtained for the CF$_2$ and CF regions were obtained consistent with the expected structure. Similarly, the broad dominant band in the C-F stretching region of the infrared is typical of that found in fluoroalkanes.

EXAMPLE 3

Perfluoro t-butyl cyclohexane

Tertiary-butyl cyclohexane (Pfaltz and Bauer Inc. Stamford, CT.) was perfluorinated by the methods described in example 1, utilizing the reaction conditions listed in Table 3. Product analysis indicated the following: infrared analysis showed typical broad dominant band in C-F stretching region from 1345 cm$^{-1}$ to 1150 cm$^{-1}$ with other peaks respective of perfluoro alkanes; the mass spectrum gave peaks at 481 (parent minus one fluorine;) 28, (perfluoro cyclohexyl group), 219 (perfluoro tertiary butyl group), and 69 (largest peak from CF$_3$ groups); $^{19}$F NMR indicated a resonance at −74 from (CF$_3$)C group, many resonances from −117 to −148 indicative of perfluoro cyclohexane group, and a resonance at −185 due to C-F at tertiary carbon connecting the cyclohexane to tertiary butyl group. All resonances were as expected for this compound.

EQUIVALENTS

Those skilled in the art will recognize, or be able to ascertain using no more than routine experimentation, many equivalents to the specific embodiments of the invention described herein. Such equivalents are intended to be encompassed by the following claims.

TABLE 3

| | Reaction Conditions Perfluoro-t-butyl cyclohexane | | | | | |
|---|---|---|---|---|---|---|
| Time Hours | Helium cc/min | F$_2$ cc/min | Zones & Temp (°C.)* | | | |
| | | | 1 | 2 | 3 | 4 |
| 24 | 30 | 1.5 | −78 | −78 | −78 | −78 |
| 24 | 10 | 1.5 | −78 | −78 | −78 | −78 |
| 24 | 10 | 1.5 | RT | −78 | −78 | −78 |
| 24 | 0 | 1.5 | RT | −78 | −78 | −78 |
| 24 | 0 | 1.5 | RT | RT | −78 | −78 |
| 24 | 0 | 1.5 | RT | RT | RT | −78 |
| 48 | 0 | 1.5 | RT | RT | RT | RT |
| 24 | 10 | 1.5 | RT | RT | RT | RT |
| 24 | 20 | 1.5 | RT | RT | RT | RT |

*RT = Room Temperature

I claim:
1. Perfluorinated tetracyclohexylmethane.
2. Perfluorinated dicyclohexylmethane.

* * * * *